(12) United States Patent
Levchik et al.

(10) Patent No.: US 7,449,526 B2
(45) Date of Patent: Nov. 11, 2008

(54) OLIGOMERIC, HYDROXY-TERMINATED PHOSPHONATES

(75) Inventors: Sergei V Levchik, Croton on Hudson, NY (US); Sophia Dashevsky, Monroe Township, NJ (US); Edward Weil, New York, NY (US); Qiang Yao, Brooklyn, NY (US)

(73) Assignee: Supresta U.S. LLC, Ardsley Park, NY (US)

( * ) Notice: Subject to any disclaimer, the term of this patent is extended or adjusted under 35 U.S.C. 154(b) by 348 days.

(21) Appl. No.: 10/491,690

(22) PCT Filed: Oct. 4, 2002

(86) PCT No.: PCT/US02/31917

§ 371 (c)(1),
(2), (4) Date: Aug. 28, 2004

(87) PCT Pub. No.: WO03/029258

PCT Pub. Date: Apr. 10, 2003

(65) Prior Publication Data

US 2005/0020800 A1 Jan. 27, 2005

(51) Int. Cl.
*B32B 27/04* (2006.01)
*B32B 27/18* (2006.01)
*B32B 27/38* (2006.01)
*C08L 63/02* (2006.01)
*C08L 63/04* (2006.01)

(52) U.S. Cl. .............. 525/523; 428/297.4; 428/413; 428/414; 428/416; 525/480

(58) Field of Classification Search .............. None
See application file for complete search history.

(56) References Cited

U.S. PATENT DOCUMENTS

| | | | |
|---|---|---|---|
| 2,435,252 A | 2/1948 | Dock Fen Toy | |
| 2,682,522 A | 6/1954 | Coover | |
| 2,716,101 A | 8/1955 | Coover | |
| 2,891,915 A | 6/1959 | McCormack et al. | |
| 3,326,852 A | 6/1967 | Thomas | |
| 3,719,727 A | 3/1973 | Masai et al. | |
| 3,829,405 A | 8/1974 | Cohen et al. | |
| 3,830,771 A | 8/1974 | Cohen et al. | |
| 3,925,303 A | 12/1975 | Rio et al. | |
| 3,932,351 A | 1/1976 | King | |
| 4,033,927 A | 7/1977 | Borman | |
| 4,035,442 A | 7/1977 | Dunworth ............ | 260/860 |
| 4,148,820 A * | 4/1979 | Evans ................ | 558/268 |
| 4,152,373 A | 5/1979 | Honig et al. | |
| 4,203,296 A | 5/1980 | Tanaka et al. | |
| 4,229,552 A | 10/1980 | Shiozaki et al. | |
| 4,331,614 A | 5/1982 | Schmidt et al. | |
| 4,332,921 A | 6/1982 | Schmidt et al. | |
| 4,415,719 A | 11/1983 | Schmidt et al. | |
| 4,632,973 A | 12/1986 | Beck ................. | 528/98 |
| 4,719,279 A | 1/1988 | Kauth et al. | |
| 4,970,249 A | 11/1990 | Joswig et al. | |
| 5,919,844 A | 7/1999 | Shimizu et al. ........ | 523/457 |
| 6,043,305 A | 3/2000 | Harris et al. ......... | 524/123 |
| 2006/0142427 A1 * | 6/2006 | Levchik et al. ........ | 523/400 |

FOREIGN PATENT DOCUMENTS

| | | |
|---|---|---|
| CA | 1335680 | 5/1995 |
| DE | 31 39 958 A1 | 4/1983 |
| DE | 3139958 | 4/1983 |
| FR | 1438381 | 3/1965 |
| FR | 2348197 | 11/1977 |
| GB | 1308521 | 2/1973 |
| JP | 72 39 154 | 12/1972 |
| JP | 2001/19746 | 1/2001 |
| JP | 2001-19746 | 1/2001 |
| JP | 2001-19746 A * | 1/2001 |
| JP | 2002-088138 | 3/2002 |

OTHER PUBLICATIONS

CAPLUS accession No. 2002:233112 for Japanese Patent No. 2002-88138 A, Ogawa et al., Mar. 27, 2002, two pages.*
Derwent accession No. 2002-447907 for Japanese Patent No. 2002-88138 A, Ogawa et al., Mar. 27, 2002, one page.*
EP Abstract of JP 2001/19746.
Chemical Abstracts, vol. 81, No. 22, Dec. 2, 1974, Abstract No. 1374821.
Orito, Zenichi et al: "Fire Resistant Polyesters Moldings" & JP 49-005454, Jan. 18, 1974.
Robert W. Stackman-Ind. Eng. Chem. Prod. Res. Dev. (1982), 21, 332-336.
H. W. Coover et al., Ind. Eng. Chem. 52 (5), 409 (1960).
Y. Imai et al. , J. Polym. Sci. Polym. Chem. Ed.
A. Natansohn, J. Appl. Polym. Sci. 32,2961 (1986).
K. S. Kim, J. Appl. Polym. Sci.28, 1119 (1983).
C. E. Carraher, Jr. , Inorg. Macromol. Rev. 1,287 (1972).
M. Schmidt et al. , Angew. Makromol. Chem. 132,1 (1985).
Anonymous, New Sci. 419 (Nov. 10, 1983).

* cited by examiner

*Primary Examiner*—Robert Sellers
(74) *Attorney, Agent, or Firm*—Dilworth & Barrese, LLP

(57) ABSTRACT

Epoxy resins that are suitable for forming epoxy laminates that meet a UL-94 rating of V-0 comprise a hydroxy-terminated oligomeric phosphonate comprising the repeating structure —OP(=O)(R)OArylene-, where R is alkyl, as a flame retardant.

17 Claims, No Drawings

OLIGOMERIC, HYDROXY-TERMINATED PHOSPHONATES

The reaction of a phosphonyl dichloride with a diol produces in most cases aliphatic phosphonic structures (1,) with the polymers are low melting and hydrophilic. Industrial interest has been concentrated on the polyphosphonates made from aromatic diols or aromatic phosphonyl dichlorides. Early studies showed that high molecular weight polyesters can be attained with carefully purified reactants and precise stoichiometry.

Because of the commercial availability of phenylphosphonyl dichloride (benzene phosphorus oxydichloride, BPOD), much work has been done on this intermediate to make polymeric phosphonates, including flame-retardant additives for poly(ethylene terephthalate) (2), poly(phenylene oxide)-polystyrene blends (3), and other thermoplastics.

Polyphenylphosphonates can be made from hydroquinone or resorcinol (4–8), tetrabromobisphenol A (9), tetrabromobisphenol and sulfonylbisphenol (10), neopentylene glycol (11), 4,4'-dihydroxybiphenyl or 4,4'-bis(4-hydroxyphenyl) fluorene (12), and 2,2'-bis(bromomethyl)-1,3-propanediol (13). Polymeric alkyl- and arylphosphonates of various bisphenols promote flame retardancy in polyacrylonitrile and nylon-6,6 (14). Copolycondensation products from resorcinol and phenylphosphonic dichloride and phenyl phosphorodichloridate are flame retardants for thermoplastic polyesters (14, 15). Toyobo introduced such a polymer in Japan for polyester fibers to meet the Japanese flame-retardant regulations for home furnishings (16, 17).

Interfacial polycondensations for the synthesis of polyphosphonates are very rapid and, under favorable conditions, give high molecular weights (18).

Transesterification of a Phosphonate with a Diol: This method is complicated with O,O-dialkyl phosphonates by side reactions in which the phosphonate acts as an alkylating agent. However, with O,O-diaryl phosphonates, ester exchange is an effective route to polymeric phosphonates (19–22):

Higher molecular weights can be attained by adding tri- or tetrahydric phenols or triaryl phosphates to the reaction mixture (23). A transparent poly(methylphosphonate) thermoplastic made by this technology was reported to be in development at one time by Bayer for use in flame-retardant aircraft applications, as well as for windshields, goggles, and police riot-control shields (21, 24). Their mechanical properties are excellent, although resistance to hot water may be somewhat deficient (21). These polyphosphonates can be mixed with polycarbonates to make flame-retardant polymer blends (22). By inclusion of diphenyl carbonate in the transesterification, copolycondensed polyphosphonate carbonates can be made (21,); these were possibly, at one time, in development for aerospace applications. By transesterification of diphenyl methylphosphonate and diphenyl iso- and terephthalate with bisphenols, high molecular weight polyarylates with favorable properties as plastics were made (21).

The aryl-containing analogues to the hydroxy-terminated oligomeric phosphonate additive, which is the subject matter of the present invention, is known (25) but would be of lower phosphorus content that the additive contemplated herein.

The problems of brominated FR-containing epoxy encapsulants has been described (26). Epoxy resin compositions that are suitable for encapsulating (or sealing) a semiconductor have contained monomeric phosphoric acid ester flame retardants (27).

Finally, it is known to synthesize poly(m-phenylene methylphosphonate) by the transesterification of diphenyl methylphosphonate with resorcinol (28). However, such a product made in that manner contained phenyl end groups which would exclude reactivity of such a product with an epoxy polymer.

REFERENCES

1. U.S. Pat. No. 2,891,915.
2. R. Stackman, Ind. Eng. Chem. Prod. Res. Dev. 21, 332 (1982).
3. Ger. Offen. DE 31 39 958 A1 (Apr. 28, 1983).
4. U.S. Pat. No. 2,435,252.
5. U.S. Pat. No. 2,716,101.
6. H. W. Coover et al., Ind. Eng. Chem. 52(5), 409 (1960).
7. Jpn. Kokai 72 39,154 (Dec. 6, 1972).
8. U.S. Pat. No. 3,326,852.
9. U.S. Pat. No. 3,932,351.
10. U.S. Pat. No. 4,229,552.
11. U.S. Pat. No. 4,033,927.
12. Y. Imai et al., J. Polym. Sci. Polym. Chem. Ed. 22(6), 1259 (1984).
13. U.S. Pat. No. 3,925,303.
14. A. Natansohn, J. Appl. Polym. Sci. 32, 2961 (1986).
15. U.S. Pat. Nos. 3,829,405 and 3,830,771.
16. U.S. Pat. No. 3,719,727.
17. K. S. Kim, J. Appl. Polym. Sci. 28, 1119 (1983) and U.S. Pat. No. 4,206,296.
18. C. E. Carraher, Jr., Inorg. Macromol. Rev. 1, 287 (1972).
19. U.S. Pat. No. 2,682,522.
20. U.S. Pat. No. 4,152,373.
21. M. Schmidt et al., Angew. Makromol. Chem. 132, 1 (1985).
22. U.S. Pat. No. 4,332,921.
23. U.S. Pat. Nos. 4,331,614 and 4,415,719.
24. Anonymous, New Sci. 419 (Nov. 10, 1983).
25. Japanese Patent Publication No. 2001-19746.
26. C. S. Wang et al., "Chemistry of Stable Brominated Epoxies", Chapter 32, in ACS Symposium Series 407, 1989.
27. U.S. Pat. No. 5,919,844.
28. U.S. Pat. No. 4,035,442.

In one embodiment of the present invention there is provided a composition comprising an oligomeric hydroxy-terminated phosphonate comprising the repeating structure —OP(=O)(R) OArylene-, where R is alkyl.

In another embodiment of the present invention there is provided a thermoset resin composition comprising an oligomeric hydroxy-terminated phosphonate comprising the repeating structure —OP(=O)(R) OArylene-, where R is alkyl, optionally in the presence of another flame retardant.

The flame retarding of epoxy circuit boards and, for example, other electronic epoxy applications to a V-0 standard pursuant to the UL-94 vertical test must be done with the retention of acceptable mechanical properties, for example, glass transition temperature ($T_g$) and with acceptable resistance to delamination. Such objectives can be attained by including in such an epoxy composition an effective amount of a composition comprising an oligomeric phosphonate comprising the repeating unit —OP(O)(R)—O-Arylene- having a phosphorus content of greater than about 12%, by weight. The phosphonate species in the composition comprise those containing —OH end groups as well, possibly, of those not containing —OH end groups. The individual phosphonate species that contain —OH end groups can be monohydroxy or dihydroxy substituted. The concentration of phosphonate species in the composition that contain hydroxy end groups will range from about 20% to about 100%, based upon the total number of termination ends ("chain ends") that potentially could hold such end groups, preferably from about 50% to about 100%. The end groups can be attached to the Arylene moiety or to the phosphorus moiety, and they are reactive with the epoxy functionality in the composition to which the flame retardant is added. The preferred R group is methyl, but can be lower alkyl.

By "Arylene" is meant any radical of a dihydric phenol. The dihydric phenol preferably should have its two hydroxy groups in non-adjacent positions. Examples include the resorcinols; hydroquinones; and bisphenols, such as bisphenol A, bisphenol F, and 4,4'-biphenol, phenolphthalein, 4,4'-thiodiphenol, or 4,4'-sulfonyldiphenol. A small amount of polyhydric phenol, such as a novolac or phloroglucinol, with three or more hydroxyl groups therein can be included to increase the molecular weight.

The Arylene group can be 1,3-phenylene, 1,4-phenylene, or a bisphenol diradical unit, but it is preferably 1,3-phenylene.

Oligomers of this type, without indication of hydroxy end groups, are known in the art and have been described as flame retardants in certain thermoplastics (as described in the prior art section at end of this document).

The oligomers of the invention can be made by any of several routes: (1) reaction of an $RPOCl_2$ with HO-Aryl-OH or a salt thereof, where R is lower alkyl, preferably methyl; (2) reaction of diphenyl alkylphosphonate, preferably methylphosphonate, with HO-Arylene-OH under transesterification conditions; (3) reaction of an oligomeric phosphite with repeating units of the structure —OP(OR')—O-Arylene- with an Arbuzov rearrangement catalyst, where R' is lower alkyl, preferably methyl; or (4) reaction of an oligomeric phosphite with the repeating units having the structure —OP(O—Ph)—O-Arylene with trimethyl phosphite and an Arbuzov catalyst or with dimethyl methylphosphonate with, optionally, an Arbuzov catalyst-. The —OH end groups, if attached to Arylene can be produced by having a controlled molar excess of the HO-Arylene-OH in the reaction media. The —OH end groups, if acid type (P—OH), can be formed by hydrolytic reactions. It is preferred that the end groups of the oligomers be mainly -Arylene-OH types.

The amount of the phosphonate flame retardant described herein can range, in an appropriate flame retarding amount, up to about 50%, by weight of the epoxy that it is intended to flame retard, preferably from about 10% to about 30%, by weight of the epoxy resin. The additive can be employed by being cured with the epoxy (e.g., in a one-pot reaction, if desired). Alternatively, the phosphonate flame retardant can be pre-reacted with the epoxy resin in a manner analogous to what is done with tetrabromobisphenol A and epoxy (as described in U.S. Pat. Nos. 6,214,468 and 6,329,474).

This invention is also useful in other epoxy formulations, including in epoxy encapsulant compositions for use in electronic applications in place of, for example, brominated flame retardants. Additionally, the compositions of this invention can also be used in structural and coating epoxy resin formulations.

If desired, the phosphonate flame retardant additive can be made, in accordance with known techniques, by utilizing a molecular weight elevating amount of a phosphate to give a more branched composition.

Also, the phosphonate compositions described herein can be used with other complementary flame retardants that are known to the person of ordinary skill in the art including, alumina trihydrate, magnesium hydroxide, ammonium polyphosphate, melamine, melamine phosphate, melamine pyrophosphate, melamine polyphosphate, melamine cyanurate, red phosphorus, triphenyl phosphate, or a bisphosphate flame retardant (such as resorcinol bis(diphenyl phosphate) or bisphenol A bis(diphenyl phosphate).

The epoxy resin of this invention can contain other components conventionally used, such as polyphenylene oxide, imide, phenolic, and bisoxazine resins.

The following Examples, which should not be construed in a limiting fashion, further illustrate the invention.

EXAMPLE 1

In this run, 124 g (0.5 mol) of diphenyl methyl-phosphonate, 113 g (1.03 mol) of resorcinol and 0.54 g of sodium methylate were heated and stirred in a reaction flask at 230° C. The reaction flask was provided with an about 40 cm-high Vigreux column wrapped with electrical heating tape and insulation to keep the phenol and any volatilized resorcinol from solidifying in the column. Vacuum was gradually dropped from 625 mm to 5 mm Hg. The reaction stopped after four hours. Phenol was distilled off during reaction, and 93 g of distillate (about 1 mol if calculated as phenol) was collected in the cold trap with 241 g remaining in the reaction flask. The distillate appeared to be almost pure phenol.

Characterization: The sample was a coffee-colored dark, but transparent, viscous liquid. It was pourable when warm and was soluble in 2-butanone and DMSO. Titration by tetrabutylammonium hydroxide to azo violet end point indicated an equivalent weight of 158 per OH group. Assuming there are two OH end group, then the molecular weight will be 158×2=316. The theoretical value was 280, indicating oligomer formation of a very low polymerization degree. The $^{31}P$ NMR spectrum showed a series of peaks between 25.7 and 27.5 ppm. These data support a structure that is mainly of the structure $CH_3P(=O)(OC_6H_4OH)_2$ with some of the structure $HOC_6H_4OP(=O)(CH_3)OC_6H_4OP(=O)(CH_3)OC_6H_4OH$ and only a small percentage of remaining phenoxy groups.

EXAMPLE 2

In this synthesis, 200 g (0.8 mol) of diphenyl methylphosphonate (DPMP), 89 g (0.8 mol) of resorcinol and 0.43 g of sodium methylate were reacted at 245° C. The temperature was gradually raised to 260° C. over the course of three and one half hours. During the reaction 141 g of condensate was collected in the trap and was found to be almost pure phenol, evidenced by the infrared spectrum. This suggests that 94% of the phenoxy groups in DPMP had been displaced by resorcinol. About 136 g of product remained in the reaction flask. The final product was a clear light amber glassy solid.

Characterization: The sample was soluble in acetone, methanol, chloroform and 2-butanone. Its infrared spectrum showed a small peak in the region of —OH group absorption.

The $^1H$ NMR showed chemical shifts for $PCH_3$ (d, 3 protons, 1.77 ppm, $CDCl_3$) and Ar—H (m, 4 protons, 7.0–7.4). A reasonable structure fitting this data is an oligomer with the repeating unit —OP(=O) $(CH_3)OC_6H_4$— with $HOC_6H_4$— and some $C_6H_5$— end groups.

EXAMPLE 3

In this synthesis, 170 g (0.69 mol) of diphenyl methylphosphonate, 72 g (0.65 mol), 0.20 g ($0.61 \times 10^{-3}$ mol) of triphenyl phosphate, and 0.025 g of sodium methylate were heated at 240 C for six and one half hours. Vacuum applied to remove phenol was gradually dropped from 625 mm to 0.3 mm Hg and, at the same time, the temperature was gradually raised to 260° C. over the course of five hours. About 137 g of phenol was collected in the trap, whereas 103 g of product remained in the reaction flask. The final product was a clear light yellow solid, which was pourable at 80° C.

Characterization: The product was soluble in acetone, 2-butanone and DMF. Titration in DMF solution by tetrabutylammonium hydroxide gave an equivalent weight for OH end groups of about 650.

EXAMPLE 4

To a three-necked flask equipped with thermometer, magnetic stirrer, distillation head and nitrogen inlet 163 g (0.52 mol) of triphenyl phosphite and 1.0 mL of methyl iodide were charged. Then, 32.7 g (0.26 mol) of trimethyl phosphite was added drop-wise at 100–110° C. over the course of one hour. The reaction temperature was then raised to 210° C. and an exothermic reaction was observed. The reaction temperature was maintained at 230° C. for two hours, and the reaction mixture was analyzed before it underwent transesterification. Diphenyl methylphosphonate was obtained as a liquid. The $^{31}$P NMR (CDCl$_3$) indicated 95% diphenyl methylphosphonate. The impurities included triphenyl phosphate (0.8%, δ=−16.4 ppm), trimethyl phosphate (0.6%, δ=−10.3 ppm), and unknown compounds (δ=19.8, 20.4. 28.4 ppm). The acid number of this crude diphenyl methylphosphonate was 5.4 mg KOH/g Then, 86 g (0.78 mol) of resorcinol and 0.024 g ($4.4 \times 10^{-4}$ mol) of sodium methoxide was charged to the above-described reaction mixture. The resulting transesterification reaction was performed at 215° C. to 230° C. for eighteen hours. Vacuum was applied after four hours to remove the phenol. Phenol was collected (130 g), whereas 148 g of product remained in the reaction flask. This final product, was a dark reddish solid, which was pourable when heated above 100° C.

Characterization: Titration of the sample with tetrabutylammonium hydroxide gave an equivalent weight of 978 to the end point determined by either azo violet indicator or the potentiometric method. The $^{31}$P NMR showed multiple peaks between δ 25 and 31 ppm, and $^1$H NMR suggested several kinds of methylphosphonate structures in the final product.

EXAMPLE 5

To a three-necked flask equipped with thermometer, magnetic stirrer, distillation head and nitrogen inlet was charged 148 g (0.48 mol) of triphenyl phosphite, 0.9 mL of methyl iodide and 31 g (0.25 mol) of dimethyl methylphosphonate at 110° C. The reaction temperature was gradually raised. At 210° C. a rapid exothermic reaction lasting about fifteen minutes was observed. The reaction mixture was stirred further for one hour at 230° C. The crude diphenyl methylphosphonate was a colorless transparent liquid mixture. The $^{31}$P NMR (CDCl$_3$) showed 93% diphenyl methylphosphonate. The impurities included triphenyl phosphate (0.3%, δ=−16.4 ppm) and unknown compounds (δ=19.8 (2.8%), 20.4 (2.8%). 28.4 (1.0%)ppm). The acid number of this crude diphenyl methylphosphonate was 8.1 mg KOH/g.

Then, 80 g (0.73 mol) of resorcinol and 0.040 g ($7.4 \times 10^{-4}$ mol) of sodium methoxide was charged to the above-described reaction mixture. The transesterification reaction was performed at 205° C. to 230° C. for eighteen hours. Vacuum was applied after four hours to remove the phenol, and 130 g of phenol was collected. About 120 g of product remained in the reaction flask.

The product was a transparent yellowish viscous solid, which was pourable above 100° C. Titration by tetrabutylammonium to the end point determined by either azo violet indicator or the potentiometric method hydroxide gave an equivalent OH weight of 3000. The $^{31}$P NMR of the sample showed small multiple peaks between δ 25 and 31 ppm, and $^1$H NMR suggested mainly three kinds of methylphosphonate structures.

EXAMPLE 6

In this run, 146.8 g (0.59 mol) of purified diphenyl methylphosphonate, 65.41 g (0.59 mol) of hydroquinone and 0.17 g of sodium methylate were reacted at 225° C. for ten and one half hours. The reactor was provided with an about 40 cm-high Vigreux column wrapped with electrical heating tape and insulation to keep the phenol and any volatilized resorcinol from solidifying in the column. Vacuum was applied to remove phenol from the reaction mixture, and it gradually dropped after two hours from 625 mm to 5 mmHg. About 106 g of material was collected in the trap and was found to be almost pure phenol, as evidenced by its NMR spectrum. About 105 g of material remained in the reaction flask. The final product was a clear light amber-yellow glassy solid, which was pourable above 90° C.

Characterization: The potentiometric titration of the sample by tetrabutylammonium hydroxide in DMF solution gave an equivalent OH weight of 9200. Its acid number by alcoholic KOH titration to p-naptholbenzein end point was 9.70 mg KOH/g.

EXAMPLE 7 (Evaluation in Epoxy Resins)

Preparation of laminates: The fire retardant additives from Examples 1–6 and epoxy was dissolved in 30% of 2-butanone at 60 C. Then, 1 wt % of 2-methyl imidazole (AMI-2 brand, from Air Products) was added. The resultant warm varnish was applied to a glass fiber mat (7628, BGF, 0.17 mm). The prepreg was dried at room temperature overnight and then at 90° C. for thirty minutes. A nontacky, transparent prepreg was obtained. Eight layers of the prepreg were stacked, sided with copper foil (0.035 mm thick), precured for thirty minutes at 130° C. and 8 MPa pressure and then cured for sixty minutes at 171 C and 30 MPa pressure.

Test Procedure: The flammability of the prepregs was measured by the standard UL 94-tests (vertical protocol). The glass transition temperature was measured by TMA according to the IPC TM-650 2.4.24 standard. The time to delamination was measured by TMA at 260° C. according to the IPC TM-650 2.4.24.1 standard.

The results of these tests are shown in Table 1, which follows.

TABLE 1

Flammability and thermal properties of laminates

|  | 7-1 | 7-2 | 7-3 | 7-4 | 7-5 | 7-6 | 7-7 | 7-8 | 7-9 | 7-10 | 7-11 |
|---|---|---|---|---|---|---|---|---|---|---|---|
| Epoxy 1[a] | 69 |  |  | 69 |  |  |  |  |  |  |  |
| Epoxy 2[b] |  | 69 |  |  | 69 | 74 | 79 |  |  |  | 69 |
| Epoxy 3[c] |  |  | 69 |  |  |  |  | 69 | 69 | 69 |  |
| Product Ex. 1 | 30 | 30 | 30 |  |  |  |  |  |  |  |  |
| Product Ex. 2 |  |  |  | 30 | 30 | 25 | 20 |  |  |  |  |
| Product Ex. 3 |  |  |  |  |  |  |  | 30 |  |  |  |
| Product Ex. 4 |  |  |  |  |  |  |  |  | 30 |  |  |

TABLE 1-continued

Flammability and thermal properties of laminates

|  | 7-1 | 7-2 | 7-3 | 7-4 | 7-5 | 7-6 | 7-7 | 7-8 | 7-9 | 7-10 | 7-11 |
|---|---|---|---|---|---|---|---|---|---|---|---|
| Product Ex. 5 |  |  |  |  |  |  |  |  |  | 30 |  |
| Product Ex. 6 |  |  |  |  |  |  |  |  |  |  | 30 |
| Catalyst AMI-2 | 1 | 1 | 1 | 1 | 1 | 1 | 1 | 1 | 1 | 1 | 1 |
| UL 94 | V-1 | V-0 | V-1 | V-1 | V-0 | V-0 | V-0 | V-0 | V-0 | V-0 | V-0 |
| $T_g$, ° C. | 110 | 135 | 135 | 130 | 160 | 190 | 135 | 163 | 140 | 157 | 140 |
| Delamination, 260° C. | Pass | Pass | Pass | Pass | Pass | Pass | Pass | Pass | Pass | Pass | Fail |

[a]Bisphenol A epoxy resin
[b]Phenol-novolac epoxy resin.
[c]Cresol-novolac epoxy resin.

We claim:

1. A thermoset resin composition comprising an oligomeric hydroxy-terminated phosphonate comprising the repeating structure —OP(=O)(R) OArylene-, where R is alkyl, optionally in the presence of another flame retardant.

2. A composition as claimed in claim 1 wherein the content of oligomeric hydroxy-terminated phosphonate ranges from about 20% to about 100%, based upon the total number of termination ends that potentially could hold such end groups, preferably from about 50% to about 100%.

3. A composition as claimed in claim 1 wherein Arylene is 1,3-phenylene.

4. A composition as claimed in claim 1 wherein R is lower alkyl.

5. A composition as claimed in claim 1 wherein Arylene is 1,3 phenylene and R is lower alkyl.

6. A composition as claimed in claim 1 wherein Arylene is 1,3-phenylene and R is methyl.

7. A composition as claimed in claim 1 wherein Arylene is a bisphenol diradical unit.

8. A composition as claimed in claim 1 wherein Arylene is a bisphenol diradical unit and R is methyl.

9. A composition as claimed in any of claims 1–8 wherein the thermoset resin is an epoxy resin, optionally wherein the oligomeric hydroxy-terminated phosphonate and the epoxy have been prereacted with one another.

10. An epoxy laminate meeting a flame retardant UL-94 rating of V-0 and resistant to delamination which comprises a flame retarding amount of the oligomeric hydroxy-terminated phosphonate as claimed in claim 1.

11. An epoxy laminate meeting a flame retardant UL-94 rating of V-0 and resistant to delamination which comprises a flame retarding amount of the oligomeric hydroxy-terminated phosphonate as claimed in claim 2.

12. An epoxy laminate meeting a flame retardant UL-94 rating of V-0 and resistant to delamination which comprises a flame retarding amount of the oligomeric hydroxy-terminated phosphonate as claimed in claim 3.

13. An epoxy laminate meeting a flame retardant UL-94 rating of V-0 and resistant to delamination which comprises a flame retarding amount of the oligomeric hydroxy-terminated phosphonate as claimed in claim 4.

14. An epoxy laminate meeting a flame retardant UL-94 rating of V-0 and resistant to delamination which comprises a flame retarding amount of the oligomeric hydroxy-terminated phosphonate as claimed in claim 5.

15. An epoxy laminate meeting a flame retardant UL-94 rating of V-0 and resistant to delamination which comprises a flame retarding amount of the oligomeric hydroxy-terminated phosphonate as claimed in claim 6.

16. An epoxy laminate meeting a flame retardant UL-94 rating of V-0 and resistant to delamination which comprises a flame retarding amount of the oligomeric hydroxy-terminated phosphonate as claimed in claim 7.

17. An epoxy laminate meeting a flame retardant UL-94 rating of V-0 and resistant to delamination which comprises a flame retarding amount of the oligomeric hydroxy-terminated phosphonate as claimed in claim 8.

* * * * *